United States Patent [19]
Mobley et al.

[11] Patent Number: 6,004,784
[45] Date of Patent: Dec. 21, 1999

[54] FERMENTATION MEDIUM AND METHOD FOR PRODUCING α, ω - ALKANEDICARBOXYLIC ACIDS

[75] Inventors: David Paul Mobley, Schenectady, N.Y.; Gary Keith Shank, Rocky Hill, Conn.

[73] Assignee: General Electric Co., Schenectady, N.Y.

[21] Appl. No.: 09/152,386

[22] Filed: Sep. 14, 1998

[51] Int. Cl.$^6$ .................. C12P 7/64; C12P 7/44; C12N 1/14; C12N 1/16
[52] U.S. Cl. .............. 435/134; 435/137; 435/142; 435/145; 435/171; 435/254.22; 435/256.8
[58] Field of Search ................ 435/134, 137, 435/142, 145, 171, 256.8, 254.22

[56] References Cited

U.S. PATENT DOCUMENTS

| | | | |
|---|---|---|---|
| 3,669,840 | 6/1972 | Hatcher | 435/137 |
| 5,254,466 | 10/1993 | Picataggio et al. | 435/142 |
| 5,620,878 | 4/1997 | Picataggio et al. | 435/142 |

*Primary Examiner*—Herbert J. Lilling
*Attorney, Agent, or Firm*—Noreen C. Johnson; Douglas E. Stoner

[57] ABSTRACT

This invention describes a low cost biofermentation medium, and an economical method using the medium, for the manufacture of α, ω-alkanedicarboxylic acids. The invention provides a biofermentation medium and a method of bioproduction for these important diacids which makes their large scale commercial production economically feasible using a biocatalyst. This method of production obviates the need for chemical synthesis using expensive starting materials from fossil fuels, and does not generate a costly hazardous waste stream.

14 Claims, No Drawings

FERMENTATION MEDIUM AND METHOD FOR PRODUCING α, ω -ALKANEDICARBOXYLIC ACIDS

This invention was made with Government support under Government Contract No. 93-COOP-1-9547, awarded by the Department of Agriculture. The Government has certain rights in this invention.

TECHNICAL FIELD

The present invention relates to the field of biofermentative production of α, ω-alkanedicarboxylic acids. In particular, the invention provides a medium and a method which achieve superior specific production of α, ω-alkanedicarboxylic acids at a low cost using a yeast biocatalyst.

BACKGROUND ART

Long-chain α, ω-alkanedicarboxylic acids (i.e., alkanedicarboxylic acids with a carbon number of nine or greater) are used as raw materials in the synthesis of a variety of chemical products and polymer materials. For example, dodecanedioic acid is used as a comonomer with bisphenol A to produce a copolyestercarbonate, a particularly desirable engineering thermoplastic which retains high impact strength, the hallmark of polycarbonate resin, while having a lower melt viscosity. This property results in better molding productivity than conventional polycarbonate resin, allowing the production of light, strong, thin-walled plastic parts.

Diacids with carbon numbers greater than four (hereinafter referred to as diacids) are currently produced almost exclusively by nonbiological conversion processes. Dodecanedioic acid is manufactured through the nickel-catalyzed cyclic trimerization of butadiene, followed by hydrogenation to cyclododecane, air oxidation to a mixture of cyclododecanone and cyclododecanol, and finally, nitric acid oxidation to dodecanedioic acid. These types of chemical processes for the production of diacids have a number of limitations and disadvantages. Each process is restricted to the production of diacids of specific carbon chain lengths, based on the starting material used. For example, the dodecanedioic acid process begins with butadiene, therefore the products of this reaction process are limited to acids with chain lengths in multiples of four. In practice, only a single diacid, dodecanedioic acid, is made by this process. In addition, the processes are based on nonrenewable petrochemical feedstocks, and the multireaction conversion process produces unwanted byproducts which result in yield loses, heavy metal wastes, and nitrogen oxides which must be destroyed in a reduction furnace.

Biological conversion processes for the production of diacids have a number of potential advantages relative to the existing non-biological conversion processes. Primary among these is the use of renewable feedstocks as starting materials and the ability to produce the diacid without the generation of hazardous chemical byproducts which necessitate costly waste disposal processes. Another important advantage achieved by using a biological process is that such a process can easily be adapted to produce a wide variety of diacids using the same biocatalyst and the same equipment. Because current organic chemical syntheses are suited to the production of only a single diacid, the synthesis of several different diacids would require the development of a new synthetic scheme for each diacid. On the other hand, a yeast biocatalyst can be used to produce diacids of varying lengths using the same equipment, media and protocols merely by providing a different substrate to the yeast.

Several naturally occurring yeasts are known to produce diacids when provided fatty acids, fatty acid esters or alkanes as substrates. Yeasts belonging to the genus Candida, such as *C. albicans, C. cloacae, C. guillermondii, C. intermedia, C. lipolytica, C. maltosa, C. parapsilosis, C. zeylenoides*, and *C. tropicalis* have been reported to produce diacids. These yeasts have a number of limitations preventing their use for the commercial production of diacids, however. They produce an inefficient total yield of diacid relative to the fatty acid or alkane starting material, and they also produce relatively large quantities of unwanted byproducts.

In yeast, n-alkane substrates are transported into the cell, hydroxylated to fatty alcohols by a specific cytochrome P450 system, and then further oxidized by an alcohol oxidase and an aldehyde oxidase to form a fatty acid. Fatty acids are oxidized in the same way to form the corresponding diacid. Both fatty acids and diacids can be degraded, however, through the peroxisomal □-oxidation pathway subsequent to activation to an acyl-CoA ester. This leads to shortening of the chain by units of two. Thus, diacids produced in yeasts are often shortened to differing degrees.

Genetically modified strains of *Candida tropicalis* have been developed that overcome some of these obstacles to cost-effective commercial production of diacids. U.S. Pat. No. 5,254,466 discloses the genetic modification of a *C. tropicalis* strain. In this strain of yeast, the beta-oxidation pathway is blocked, resulting in the production of substantially pure diacid without the unwanted conversion of the substrate into shorter chain diacids and biomass, and in substantially quantitative yield with respect to the starting material. A particular organism blocked for □-oxidation is *C. tropicalis* H5343 (ATCC No. 20962).

*C. tropicalis* has been further modified, as described in U.S. Pat. No. 5,620,878. This reference discloses amplification of the genes encoding cytochrome P450 monooxygenase and NADPH reductase, which results in increased 4-hydroxylase activity and thus increased specific productivity (grams of diacid/liter/hr) of diacids. The particular organism having amplified cytochrome P450 monooxygenase and NADPH reductase components is known as *C. tropicalis* AR40 (ATCC No. 20987).

The known genetically modified strains show distinct advantages over previously available yeast strains for the production of diacids. This technology has resulted in organisms which are able to produce the large quantities of product necessary to develop a commercially feasible process. The described production using these prior art methods, however, includes the use of preferred fermentation media which contain relatively expensive components. The cost of the medium in the biofermentation processes is too high for practical use in diacid production on a large commercial scale. For example, the preferred embodiment of U.S. Pat. No. 5,620,878 describes a medium comprising 3 g/L peptone, 6 g/L yeast extract, 6.7 g/L Yeast Nitrogen Base (Difco), 3 g/L sodium acetate, 7.2 g/L $K_2HPO_4 \cdot 3H_2O$, 9.3 g/L $KH_2PO_4$, and 75 g/L glucose. These are ingredients suitable for laboratory practice, but not industrial scale fermentation.

Consequently, there remains a need for low-cost, complete biofermentation media which provide sufficient nutrient support to the yeast biocatalyst to permit high specific productivity of diacids from suitable fatty acid or alkane starting material.

SUMMARY OF INVENTION

Accordingly, the inventors have developed an economical fermentation medium and process for the manufacture of α,ω-alkanedicarboxylic acids. The invention is a biofermentation medium for the production of α,ω-alkanedicarboxylic acids which supports the growth of yeast, comprising (a) corn syrup providing a glucose concentration of about 30 to about 60 g/L; (b) an organic nitrogen source selected from the group consisting of corn steep liquor at a concentration of about 4 to about 15 g/L and brewer's yeast extract at a concentration of about 1 to about 5 g/L; (c) a source of inorganic nitrogen; (d) a source of phosphate; (e) optionally a source of trace elements; (f) an α,ω-alkanedicarboxylic acid-producing yeast culture; and (g) a substrate which the yeast can convert to an α,ω-alkanedicarboxylic acid. Through the use of low cost, alternative nutrient sources to support yeast growth, the invention provides a medium which allows important diacids to be produced commercially, in large quantity, using a biological conversion process which does not require petrochemical starting material or produce a hazardous waste stream. The invention provides a medium and method which, although far less costly than prior art media, results in diacid production at least as high as the prior art methods by the yeast cells.

DETAILED DESCRIPTION OF INVENTION

This invention provides culture media for the growth and maintenance of *C. tropicalis* AR40 and similar yeast strains. These media incorporate nutrient sources which provide a rich nutrient broth which promotes good growth of yeast cells, but which is also both less expensive than media reported in the prior art and results in high specific diacid productivity by the yeast cells.

A preferred prior art fermentation medium for diacid-producing yeast includes a carbon source such as glucose, an organic nitrogen source such as yeast extract, salts, buffers, and a source of amino acids, vitamins, and trace minerals such as Yeast Nitrogen Base (Difco). See Table 1. These media, while successful in the laboratory, are not suitable for the production of diacids commercially due to the high cost of their ingredients.

TABLE 1

Representative Prior Art Medium.[1]

| Component | Concentration (g/L) | Purpose |
| --- | --- | --- |
| Glucose | 75 | energy, carbohydrate |
| Difco Yeast Nitrogen Base | 6.7 | inorganic nitrogen, amino acids, vitamins, minerals, trace elements |
| Difco Yeast Extract | 3.0 | organic nitrogen (amino acids), vitamins, minerals, and trace elements |
| Ammonium Sulfate | 3.0 | inorganic nitrogen |
| Potassium Phosphate, monobasic | 1.0 | buffer |
| Potassium Phosphate, dibasic | 1.0 | buffer |

[1]Picataggio et al., Bio/Technology, 10:894–898 (1992).

Surprisingly, the inventors have found that substitution of lower cost nutrient sources does not reduce the viability of the yeast culture, nor does it reduce the specific production of the desired diacids.

The inventive media use corn syrup as the major carbohydrate source. The unrefined corn syrup in Media OPT1 and OPT2, see Tables 2 and 3, is a much cheaper source of glucose than the highly purified glucose used in typical prior art media for diacid-producing yeast. We also believe that unrefined corn syrup is a preferred ingredient because it also contains trace nutrients that highly purified glucose does not, although refined corn syrup or modified corn syrup may be substituted. The specific trace nutrients responsible for the improved results seen with unrefined corn syrup relative to pure glucose are unknown. Unrefined corn syrup contains low levels of minerals and metal salts such as calcium, magnesium and iron, but the specific role of these is unknown. In addition, the inventors have discovered that when the inventive media are used, an effective concentration of 40 g/L glucose provides a sufficient energy source, while about 75 g/L glucose was described in the prior art. This substitution substantially reduces the cost of the carbohydrate source in the medium.

While prior art media contain standardized and/or supplemented yeast extracts which are semi-purified and designed for standard laboratory use as a source of amino acids, corn steep liquor and brewer's yeast extract provide these nutrients in the inventive media. Typical prior art nitrogen and trace nutrient sources are Difco Yeast Extract, a standardized yeast extract containing amino acids, vitamins, minerals, and trace elements, and Difco Yeast Nitrogen Base, a prepared laboratory medium formula containing ammonium sulfate, salts of phosphate, magnesium, sodium, and calcium, along with amino acids, vitamins, and trace elements. These are relatively expensive nutrient sources, since they contain carefully controlled levels of ingredients such as B vitamins. The inventive media contain less defined components which can provide equivalent nutrition for less total cost. Preferred media contain corn syrup providing a glucose concentration of about 30 to about 60 g/L, an organic nitrogen source (corn steep liquor, about 4–15 g/L or brewer's yeast extract, about 1–5 g/L), an inorganic nitrogen source, a phosphate source, and optionally a trace element source.

The media for use with this invention may be used with any diacid-producing yeast, and a wide variety of substrates. Any fatty acid, fatty acid ester, or alkane substrate, saturated or unsaturated may be used. The substrate desirably has 6–22 carbon atoms, although fatty acids desirably have 10–22 carbon atoms. Preferred substrates are lauric acid, myristic acid, palmitic acid, stearic acid, oleic acid, palmitoleic acid and the methyl esters thereof, and dodecane, tridecane, and tetradecane.

The following examples describe media according to the invention and their use in the production of α,ω-alkanedicarboxylic acids. A comparative example using the medium containing the ingredients listed in Table 1 (with glucose at 60 g/L), is also included. This comparative example demonstrates that the media of this invention support growth and specific production of α,ω-alkanedicarboxylic acids at least as well as prior art media under the same conditions.

EXAMPLES

1. OPT1 Medium

The corn steep liquor, ammonium sulfate and phosphate salts listed in Table 2 in amounts sufficient to yield the indicated final concentrations were dissolved in deionized water and sterilized by heating to 121° C. at 15 psig. The unrefined corn syrup, as a 50% glucose solution, was sterilized separately by heating in the same way. Concentrated solutions of the remaining mineral salts and the trace elements were individually prepared and separately filter sterilized. The corn syrup, salts, and trace elements solutions were added to the cooled solution containing corn steep liquor to yield the indicated concentrations. The resulting medium was then brought to a pH of 6.5. The unrefined corn syrup used in Media OPT1 and OPT2 was Cargill CLEAR-SWEET™ Unrefined 95% Dextrose corn syrup. The corn steep liquor was Cargill Heavy Steepwater.

TABLE 2

OPT1 Medium.

| Component | Concentration (g/L) |
|---|---|
| Unrefined Corn Syrup | 40 (glucose basis) |
| Corn Steep Liquor | 9.0 |
| Ammonium Sulfate | 8.0 |
| Potassium Phosphate, monobasic | 2.0 |
| Potassium Phosphate, dibasic | 1.0 |
| Magnesium Sulfate ($MgSO_4 \cdot 7H_2O$) | 0.5 |
| Sodium Chloride | 0.1 |
| Calcium Chloride ($CaCl_2 \cdot 2H_2O$) | 0.1 |
| Trace Elements Solution* | 1.0 mL/L |

*Trace Elements Solution contains 500 mg/L $H_3BO_3$, 400 mg/L $MnSO_4 \cdot H_2O$, 400 mg/L $ZnSO_4 \cdot 7H_2O$, 200 mg/L $FeCl_3 \cdot 6H_2O$, 200 mg/L $NaMoO_4 \cdot 2H_2O$, 100 mg/L KI, and 40 mg/L $CuSO_4 \cdot 5H_2O$.

2. OPT2 Medium

OPT2 Medium contains the components listed in Table 3, and is made as described in Example 1, substituting Brewer's Yeast Extract for the Corn Steep Liquor. The brewers' yeast extract used in this medium was Amberex™ 1003.

TABLE 3

OPT2 Medium.

| Component | Concentration (g/L) |
|---|---|
| Unrefined Corn Syrup | 40 (glucose basis) |
| Ammonium Sulfate | 8.0 |
| Brewers Yeast Extract | 3.0 |
| Potassium Phosphate, monobasic | 2.0 |
| Potassium phosphate, dibasic | 1.0 |
| Magnesium Sulfate ($MgSO_4 \cdot 7H_2O$) | 0.5 |
| Sodium Chloride | 0.1 |
| Calcium Chloride ($CaCl_2 \cdot 2H_2O$) | 0.1 |
| Trace Elements Solution* | 1.0 mL/L |

*Trace Elements Solution is described in Table 2.

3. Biofermentative Production of 1,14-tetradecanedioic acid with C. tropicalis AR40 Grown on OPT1 Medium.

C. tropicalis AR40 was grown under sterile conditions on Medium OPT1 in a stirred, aerated fermentor with an initial liquid volume of 2.5 L. The sterile culture medium was inoculated with a 10% inoculum of C. tropicalis AR40 and grown at 30° C., pH 6.5, with an aeration rate of 1 wm (air) for 18 hours. At this time, after growth of the cells had reached maximum cell density, the conversion phase was begun by beginning to add methyl myristate substrate. At the same time, the pH of the culture was raised to 8.2 with 6N sodium hydroxide. The pH was maintained at 8.2 for the first 30 hours of the conversion phase and at 8.7 thereafter, by the controlled addition of sodium hydroxide solution. During the conversion phase, unrefined corn syrup was continuously added to the culture medium at the rate of 2.0 g glucose/L/hour. The substrate was added at a rate sufficient to provide an excess of substrate with respect to rate of conversion of substrate to diacid product. Over the 49 hour conversion period, the 1,14-tetradecanedioic acid was produced at an average rate of 0.76 g/L/hr.

4. Biofermentative Production of 1,14-tetradecanedioic acid with C. tropicalis AR40 Grown on OPT1 Medium.

The fermentation described in Example 3 was repeated with the following minor differences. The pH was controlled to pH 8.2 for the first 32.5 hours of the conversion and 8.7 thereafter. During the conversion phase, unrefined corn syrup was added at a rate of 1.8 glucose/L/h. Over a 50 hour conversion period, 1,14-tetradecanedioic acid was produced at an average rate of 0.99 g/L/hr.

5. Biofermentative Production of 1,14-tetradecanedioic acid with C. tropicalis AR40 Grown on OPT2 Medium.

The fermientation described in Example 4 was repeated, substituting OPT2 Medium for OPT1 Medium and at a slightly different pH. The pH was controlled to pH 8.1 for the first 29.5 hours and 8.7 thereafter. Over a 50 hour conversion period, 1,14-tetradecanedioic acid was produced at an average rate of 0.84 g/L/hr.

6. Comparative Biofermentative Production of 1,14-tetradecanedioic acid with C. tropicalis AR40 Grown on a Representative Prior Art Medium.

Biofermentation was performed four separate times using the same biocatalyst and under essentially the same conditions as Example 4, except that the medium used was the representative prior art medium described in Table 1 with glucose at 60 g/L. Also, for these examples, according to the prior art methods, reagent grade glucose was used not only as the carbon source during cell growth, but during the conversion phase as well. During conversion, the glucose was added at a rate of 1.8±0.3 g/L/hour, and the substrate was added to the fermentor at a rate sufficient to provide an excess of substrate with respect to the rate of conversion of substrate to diacid. The diacid production rate for these experiments ranged from 0.58 to 0.80 g/L/hr. The average diacid production rate over 50 hours of conversion of the four experiments was 0.69 g/L/hr.

We claim:

1. A biofermentation medium for the production of α, ω-alkanedicarboxylic acids which supports the growth of yeast, comprising:
   a) corn syrup providing a glucose concentration of about 30 to about 60 g/L;
   b) an organic nitrogen source selected from the group consisting of corn steep liquor at a concentration of about 4 to about 15 g/L and brewer's yeast extract at a concentration of about 1 to about 5 g/L;
   c) a source of inorganic nitrogen;
   d) a source of phosphate;
   e) optionally a source of trace elements;
   f) an α, ω-alkanedicarboxylic acid-producing yeast culture; and
   g) a substrate which the yeast can convert to an α, ω-alkanedicarboxylic acid.

2. A biofermentation medium according to claim 1, wherein the corn syrup provides a glucose concentration of about 40 g/L, and the organic nitrogen source is corn steep liquor at a concentration of about 9 g/L.

3. A biofermentation medium according to claim 1, wherein the corn syrup provides a glucose concentration of about 40 g/L, and the organic nitrogen source is brewer's yeast extract at a concentration of about 3 g/L.

4. A biofermentation medium according to claim 1, wherein the corn syrup is unrefined corn syrup.

5. A method of producing α, ω-alkanedicarboxylic acids comprising biofermentation by yeast of a substrate selected from the group consisting of fatty acids, fatty acid esters, and alkanes, in the biofermentation medium according to claim 1.

6. A method of producing α, ω-alkanedicarboxylic acids according to claim 5, wherein the substrate is a fatty acid.

7. A method of producing α, ω-alkanedicarboxylic acids according to claim 5, wherein the substrate is a fatty acid ester.

8. A method of producing α, ω-alkanedicarboxylic acids according to claim 5, wherein the substrate is an alkane.

9. A method of producing α, ω-alkanedicarboxylic acids according to claim 6, wherein the fatty acid substrate has 10–22 carbon atoms.

10. A method of producing α, ω-alkanedicarboxylic acids according to claim 7, wherein the alykl portion of the fatty acid ester substrate has 6–22 carbon atoms.

11. A method of producing α, ω-alkanedicarboxylic acids according to claim 8, wherein the alkane substrate has 6–22 carbon atoms.

12. A method of producing α, ω-alkanedicarboxylic acids according to claim 5, wherein the substrate is saturated.

13. A method of producing α, ω-alkanedicarboxylic acids according to claims 6 or 7, wherein the substrate is unsaturated.

14. A method of producing α, ω-alkanedicarboxylic acids according to claim 5, wherein the substrate is selected from the group consisting of lauric acid, myristic acid, palmitic acid, stearic acid, oleic acid, palmitoleic acid, lauric acid methyl ester, myristic acid methyl ester, palmitic acid methyl ester, stearic acid methyl ester, oleic acid methyl ester, palmitoleic acid methyl ester, dodecane, tridecane and tetradecane.

* * * * *

UNITED STATES PATENT AND TRADEMARK OFFICE
CERTIFICATE OF CORRECTION

PATENT NO. : 6,004,784

DATED : December 21, 1999

INVENTOR(S) : Mobley et al.

It is certified that error appears in the above-identified patent and that said Letters Patent is hereby corrected as shown below:

Col 2, line 21, cancel " ☐ -oxidation" and substitute --b-oxidation--.

Col. 2, line 34, cancel " ☐ -oxidation" and substitute --b-oxidation--.

Col. 5, line 53, cancel "1 wm" and substitute --1 vvm--.

Col. 5, line 64, after "with respect to" insert --the--,

Col. 6, line 12, cancel "fermientation" and substitute --fermentation--.

Col. 7, line 12, cancel "alykl" and substitute --alkyl--.

Signed and Sealed this

Eighth Day of August, 2000

Attest:

Attesting Officer

Q. TODD DICKINSON

Director of Patents and Trademarks